US008181278B2

(12) United States Patent  
Odorzynski et al.

(10) Patent No.: US 8,181,278 B2  
(45) Date of Patent: May 22, 2012

(54) WAIST PROTECTION GARMENT

(75) Inventors: Thomas W. Odorzynski, Green Bay, WI (US); MeeWha Lee, Appleton, WI (US); Shannon K. Melius, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2476 days.

(21) Appl. No.: 10/741,758

(22) Filed: Dec. 18, 2003

(65) Prior Publication Data

US 2005/0132476 A1   Jun. 23, 2005

(51) Int. Cl.  
*A41D 13/00* (2006.01)
(52) U.S. Cl. .......................................... 2/310
(58) Field of Classification Search .............. 2/310–318, 2/455, 338, 69, 235, 236, 229; 604/396, 604/367, 385.22, 385.23, 385.24, 385.27, 604/385.31  
See application file for complete search history.

(56) References Cited

U.S. PATENT DOCUMENTS

| | | |
|---|---|---|
| 3,555,569 A | 1/1971 | Jones |
| 3,603,316 A | 9/1971 | Lehman |
| 4,472,839 A | 9/1984 | Johansen |
| 4,663,220 A | 5/1987 | Wisneski et al. |
| 4,704,114 A * | 11/1987 | Wilson et al. ............ 604/385.22 |
| 4,798,603 A | 1/1989 | Meyer et al. |
| 4,964,860 A | 10/1990 | Gipson et al. |
| 5,135,522 A | 8/1992 | Fahrenkrug et al. |
| 5,176,668 A | 1/1993 | Bernardin |
| 5,192,606 A | 3/1993 | Proxmire et al. |
| 5,226,992 A | 7/1993 | Morman |
| H1440 H | 5/1995 | New et al. |
| 5,445,628 A | 8/1995 | Gipson et al. |
| 5,482,765 A | 1/1996 | Bradley et al. |
| 5,509,915 A | 4/1996 | Hanson et al. |
| 5,549,593 A | 8/1996 | Ygge et al. |
| 5,607,416 A * | 3/1997 | Yamamoto et al. ........... 604/397 |
| 5,640,717 A | 6/1997 | Ray |
| 5,669,901 A * | 9/1997 | LaFortune et al. ............ 604/391 |
| 5,704,933 A * | 1/1998 | Fell et al. ...................... 604/399 |
| 5,722,968 A * | 3/1998 | Datta et al. .................... 604/391 |
| 5,843,056 A | 12/1998 | Good et al. |
| 5,870,778 A * | 2/1999 | Tharpe .............................. 2/400 |
| 5,879,341 A | 3/1999 | Odorzynski et al. |
| 5,906,604 A * | 5/1999 | Ronnberg et al. ............. 604/386 |
| 5,971,970 A | 10/1999 | Carlbark et al. |
| 6,075,179 A | 6/2000 | McCormack et al. |
| 6,149,934 A | 11/2000 | Krzysik et al. |
| 6,245,051 B1 * | 6/2001 | Zenker et al. ............ 604/385.23 |
| 6,432,099 B2 * | 8/2002 | Ronnberg ..................... 604/392 |

(Continued)

FOREIGN PATENT DOCUMENTS

EP   0 217 032 B1   2/1992

(Continued)

*Primary Examiner* — Tejash Patel  
(74) *Attorney, Agent, or Firm* — Alyssa A. Dudkowski; David J. Arteman

(57) ABSTRACT

The invention relates to a waist protection garment. The waist protection garment may include: a length corresponding to the waist circumference of a wearer and the length defining two longitudinal sides; a width in a direction perpendicular to the length and the width defining two lateral sides; an outer cover including a fluid impermeable material; a liner in superposed relation to the outer cover and the liner defining a bodyfacing surface and including a liquid permeable material; and a fastener for attaching one lateral side to the other lateral side.

16 Claims, 5 Drawing Sheets

U.S. PATENT DOCUMENTS

| | | |
|---|---|---|
| 6,478,787 B1 | 11/2002 | Ihrfelt et al. |
| 6,482,194 B1 * | 11/2002 | Putzer ................ 604/385.19 |
| 6,552,245 B1 | 4/2003 | Roessler et al. |
| 6,572,601 B2 * | 6/2003 | Suprise et al. ............ 604/391 |
| 6,869,424 B1 * | 3/2005 | Morman et al. .......... 604/396 |
| 2002/0138065 A1 | 9/2002 | Yeater et al. |
| 2002/0173767 A1 | 11/2002 | Popp et al. |
| 2002/0183706 A1 | 12/2002 | Valentin et al. |

FOREIGN PATENT DOCUMENTS

| | | |
|---|---|---|
| EP | 1 009 350 B1 | 5/2003 |
| FR | 2 680 316 A1 | 2/1993 |
| WO | WO 88/07335 A1 | 10/1988 |
| WO | WO 91/08725 A1 | 6/1991 |
| WO | WO 02/34184 A1 | 5/2002 |
| WO | WO 2004/060230 A1 | 7/2004 |

* cited by examiner

WAIST PROTECTION GARMENT

BACKGROUND OF THE INVENTION

Disposable absorbent garments, such as diapers and adult incontinence articles, generally absorb and contain waste body fluids. Disposable absorbent garments generally have a body portion that may hold, or otherwise position, an absorbent core against the body of a wearer of the garment. The body portion may include a front waist region, a back waist region and a crotch region that connects the front waist region and the back waist region. These disposable absorbent garments may generally be worn to encircle the waist of the wearer. Due to the rate of insult to the garment, and/or as a result of the amount of the insult, absorbent garments may leak.

Disposable absorbent garments are manufactured in one or more sizes that typically correspond to different weight ranges of users. For example, HUGGIES disposable diapers manufactured by the Kimberly-Clark Corporation of Neenah, Wis. are sold in at least six sizes designed to accommodate different ages/sizes of children. Despite efforts to design garments to properly fit a wide spectrum of users, the disposable absorbent garments may not fit tightly, or conform closely, to the torso of the wearer. Therefore, because there may not be a complete seal around the waist of the users of such garments, there may be leakage of waste body fluids, especially during the night while the wearer is in the sleeping posture. Particularly when the wearer is in the prone position, loss of containment may occur in the front waist region. Obviously, such leakage is undesirable because it soils the wearer's clothing and potentially even their bedding. An opportunity to reduce leakage may be achieved if the garment is adapted to better conform to the waist of the wearer.

In addition to leakage that may occur through the waist edges in the front and back waist regions of disposable absorbent garments, performance of the garments may be diminished in the fasteners used for securing the garments about the waists of the wearers come undone. Disposable absorbent garments may unfasten during the course of the usual movements, e.g., associated with activity of the wearer. The wearer, e.g., an infant or child, may also, undesirably, unfasten the fasteners. Therefore, improving the security of the fasteners of the garments as well as inhibiting the undesired removal of the garments by children and infants would be desirable.

Accordingly, there remains a need for a waist protection garment for use in conjunction with disposable absorbent garments that improves the fit of the disposable absorbent garment, reduces waste leakage through the waist edges of the disposable absorbent garment and improves the security of the fasteners on the disposable absorbent garment.

SUMMARY OF THE INVENTION

The present invention relates to waist protection garments that may be used in conjunction with disposable absorbent garments. The waist protection garments of the invention include a length that generally corresponds to a waist circumference of a wearer of the garment. The length defines two longitudinal sides of the waist protection garment. The waist protection garment also includes a width in a direction generally perpendicular to the length of the garment where the width defines two lateral sides. Additionally, the waist protection garment may include an outer cover and a liner in superposed relationship to the outer cover. The outer cover may include a fluid impermeable material in order to provide a barrier. The liner may define a body-facing surface that is in contact with the wearer's skin when the waist protection garment is in use. The liner may include a liquid permeable material. The waist protection garment may also include a fastener for attaching one of the lateral sides to the other lateral side in either the front or back waist region of the wearer. The waist protection garment may be sized to accommodate the waist circumference of a variety of wearers, from infants, to small children, to adults. The waist circumference of the wearer may be generally understood to be the circular distance around the torso of a person where the waistband of pants or underwear lands. In order to provide an absorbent benefit, the waist protection garment may include an absorbent core disposed between the liner and the outer cover. The absorbent core may be provided in order to assist with the absorption of waste bodily fluids that may leak from a disposable absorbent garment with which the waist protection garment is worn.

The waist protection garments of the invention may be constructed of a variety of nonwoven and woven materials. In some aspects, the waist protection garment may be constructed of stretchable materials. In these aspects, the outer cover includes a stretchable material and correspondingly, the liner also includes a stretchable material. Stretchable materials may include materials that are extensible, that is materials that are capable of extending but have low retractive forces to return to their original lengths. Stretchable materials may also include elastic materials, such as materials that are capable of extension and are also capable of retracting to their original length when a pulling force is released. In some aspects, the waist protection garments of the invention have a length that is capable of elongating by 50% to about 200% at a load of less than or equal to about 700 grams. Such capacity for extension allows a given size of waist protection garment to fit a wider range of wearers. Desirably the waist protection garment is capable of extending freely and easily and does not have a strong retractive force that could become uncomfortable to the wearer.

An additional feature of the waist protection garments of the invention is the inclusion of a fastener. The fastener may be used to secure one lateral side of the waist protection garment to the other lateral side. A variety of fastening mechanisms are known in the art and for example, the fastener may be positioned on one lateral side and may include a hook material. The hook material on one lateral side may be engaged with or attached to the outer surface of the outer cover on the other lateral side of the waist protection garment. For example, when a fastener is positioned on one lateral side of the waist protection garment, a landing zone may be positioned on the other lateral side of the waist protection garment so that the fastener may be engaged into the landing zone. While the landing zone may include one or more known materials, the landing zone may also include a loop material capable of engaging hook materials such as those materials that are presently used as fasteners on disposable diapers and adult incontinence garments. In addition to fasteners on the lateral sides of the waist protection garment, the waist protection garment may also include fasteners along at least a portion of one or both of the longitudinal sides. An attachment mechanism may be desirable on the longitudinal sides of the waist protection garment in order to better secure the waist protection garment to the disposable absorbent garment with which the waist protection garment is used. For example, it may desirable to provide a series of individual hooks along a portion of a longitudinal side of the waist protection garment in order to engage with the waist regions of the underlying disposable absorbent garment. Such attachment mechanisms may be provided along the full length of the waist protection garment or only along a portion of the length of the waist protection garment depending on where attachment to the disposable absorbent garment is best utilized. On the portion of the waist protection garment that comes into contact with the skin of the wearer, it may be desirable to provide a different type of attachment mechanism such as a body adhesive in order to secure that longitudinal side of the waist protection garment to the wearer.

The waist protection garments of the invention may be provided in a range of sizes in order to accommodate a broad range of wearers. For example, the length of the waist protection garment of the invention may be from about 15 centimeters to about 200 centimeters. This range of length would be capable of accommodating users from small infants up to grown adults. Additionally, the width of the waist protection garments of the invention may be varied depending again on the size of the wearer. For example, the width of the waist protection garments of the invention may be from about 5 centimeters to about 20 centimeters. It may be desirable to adjust the width of the waist protection garment depending on how much overlap with the underlying disposable absorbent garment is desirable. While the width of the waist protection garment may be the same across the entire length of the waist protection garment, it is also feasible for the width to change over the length of the waist protection garment. In this case, the width would not be uniform across the length of the waist protection garment. It may be desirable to provide a nonuniform width for the waist protection garment in order to provide greater overlap with the underlying disposable garment in some regions and less overlap in other regions.

For waist protection garments of the invention in which stretchable materials are utilized, the garments may be capable of providing a greater range of fit in order to accommodate a larger number of wearers. For example, when the waist protection garment is constructed of an outer cover incorporating a stretchable material and a liner incorporating a stretchable material, the waist protection garment may have a percent fit range of greater than or equal to about 33%. More specifically, the waist protection garments of the invention may provide a percent fit range of about 50% to about 200% and in some cases, a percent fit range of about 80% to about 150%.

While for some applications it may be desirable for the waist protection garments of the invention to completely encircle the waist of the wearer, there may also be occasions when it is desirable for the waist protection garment to encircle only a portion of the total waist circumference of the wearer. Therefore the present invention also includes waist protection garments that have a length corresponding to a portion of a waist circumference of a wearer where the length defines two longitudinal sides of the garment. Such garments also have a width in a direction generally perpendicular to the length where the width defines two lateral sides. The garments may also include an outer cover, a liner in superposed relation to the outer cover, and a fastener on each lateral side. The outer cover may include a fluid impermeable material in order to provide a barrier and the liner may define a bodyfacing surface and may include a liquid permeable material. When the waist protection garment does not completely encircle the waist circumference of the wearer, it may be desirable for the waist protection garment to additionally include a fastener on at least one of the longitudinal sides of the waist protection garment. The fastener may include known fastening materials such as adhesive or hook materials. The fastener that may be provided on one of the longitudinal sides may be used to engage an underlying disposable absorbent garment. Provision of such a fastener assists with securing the waist protection garment to the underlying absorbent garment, particularly when the lateral sides are not attached to each other. Such waist protection garments may also include an absorbent core disposed between the liner and the outer cover.

In another aspect, the waist protection garments of the invention may also include garments that are continuous, that is they do not have open lateral sides. Such waist protection garments may be put on by a wearer by either pulling the waist protection garment over the wearer's head, or by pulling the waist protection garment up from the feet and over the hips of the wearer. Such waist protection garments include a circumference that corresponds generally to the waist circumference of the wearer. The circumference defines two longitudinal sides of the waist protection garment. The waist protection garment also includes a width in a direction generally perpendicular to the circumference. Desirably, continuous waist protection garments include a stretchable outer cover that may include a stretchable outer cover material. The stretchable outer cover may include a fluid impermeable material in order to provide a barrier. Such continuous waist protection garments may also include a stretchable liner provided in superposed relation to the outer cover. The liner may define a bodyfacing surface that contacts the skin of the wearer and may include a liquid permeable material. Desirably the continuous waist protection garment is constructed of stretchable materials in order to ease application over the wearer's head or over the wearer's hips. Because such waist protection garments are continuous, consideration should be given to how the waist protection garments may be readily removed from the wearer, particularly if the garment becomes soiled. In order to provide such an easy removal, the waist protection garments of the invention may include a passive bond across the width of the waist protection garment. The purpose of the passive bond is to provide a location along the circumference of the waist protection garment that can be easily torn or separated by a caregiver in order to remove the waist protection garment. Alternatively, such continuous waist protection garments may include an area that is perforated across the width of the garment in order to make removal simple and easy.

The present invention also relates to a leakage containment system. The leakage containment system may include an absorbent article and a waist protection garment that are used together. The absorbent article may include a front waist region and a back waist region. Examples of absorbent articles that may be used with the leakage containment systems of the invention include disposable diapers, training pants, swim pants and adult incontinence garments. The waist protection garment may be capable of being disposed over at least a portion of the front waist region or the back waist region of the absorbent article when it is worn. The waist protection garment may include a length that generally corresponds to the waist circumference of a wearer where the length defines two longitudinal sides of the garment. Additionally, the waist protection garment includes a width in a direction generally perpendicular to the length where the width defines two lateral sides to the garment. The waist protection garment may also include an outer cover, a liner in superposed relation to the outer cover and a fastener for attaching one lateral side to the other lateral side. The outer cover may include a fluid impermeable material in order to provide a barrier and the liner may include a liquid permeable material. Additionally, the waist protection garment of the leakage containment system may include an absorbent core disposed between the liner and the outer cover.

In an additional aspect, the present invention relates to a leakage containment system including an absorbent article and a waist protection garment capable of being disposed over at least one of a front waist region or a back waist region of the absorbent article when the absorbent article is worn. The waist protection garment of the leakage containment system may include a circumference that generally corresponds to the waist circumference of the wearer. In this aspect, the waist protection garment is a continuous piece of material so that the circumference defines two longitudinal sides to the garment. The waist protection garment also includes a width in a direction generally perpendicular to the circumference. Further, the waist protection garment includes a stretchable outer cover and a stretchable liner in superposed relation to the outer cover. The outer cover may include a fluid impermeable material and the liner may define a bodyfacing surface that comes into contact with the skin of the wearer and includes a liquid permeable material. The waist protection garment may also include a passive bond across its width in order to provide easy removal of the waist protection garment from the wearer. Alternatively, the waist protection garment may include a perforation across its width in order to easily remove the waist protection garment after use, particularly if the garment is soiled.

These aspects and additional aspects of the invention will be described in greater detail herein. Further, it is to be understood that both the foregoing general description and the following detailed description are exemplary and are intended to provide further explanation of the invention claimed. The accompanying drawings, that are incorporated in and constitute part of this specification, are included to illustrate and provide a further understanding of the disposable absorbent articles of the invention. Together with the description, the drawings serve to explain various aspects of the invention.

BRIEF DESCRIPTION OF DRAWINGS

Refer now to the figures, which are meant to be exemplary, not limiting, and wherein like elements are numbered alike in the several figures.

DETAILED DESCRIPTION

Described herein is a waist protection garment to be used in conjunction with an absorbent article (such as a diaper, training pant, an adult incontinence article, etc.). Absorbent articles may have a front waist region, a back waist region and crotch region that interconnects the front waist region and the back waist region. Absorbent articles typically have two longitudinal side edges and two waist edges in a lateral direction. When the absorbent article is worn, the two waist edges form an opening around the waist of a wearer. The waist protection garment may include an outer cover (which may be stretchable), a liner material and a fastener. The waist protection garment may optionally include an absorbent core between the outer cover and the liner. The waist protection garment is desirably adjustable, and may be reusable. The waist protection garment is designed to create an additional seal around the waist edges of the absorbent article with which it is used. The waist protection garments of the present invention provide a barrier that improves the containment function of absorbent articles, thereby reducing leakage.

While the waist protection garments of the invention may be used with a variety of disposable absorbent garments, the waist protection garments will be described in the context of use with a disposable diaper such as may be worn by an infant or toddler. Examples of diaper configurations suitable for use in connection with the instant application are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference.

Figure 3:
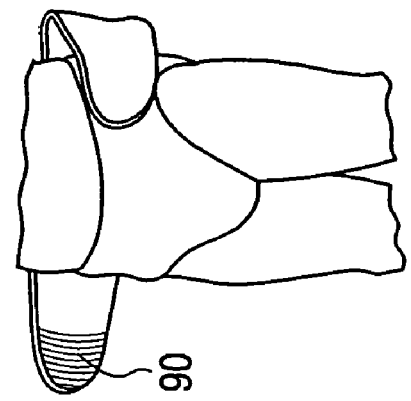
FIG. 3 is an exemplary embodiment of a waist protection garment of the invention disposed about the torso of a wearer, fastened in the back waist region.
Figure 2:
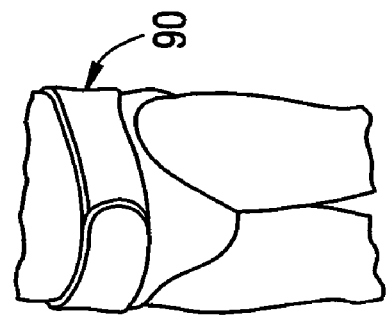
FIG. 2 is an exemplary embodiment of the waist protection garment of FIG. 1 disposed about the torso of a wearer, fastened in the front waist region.
Figure 1:
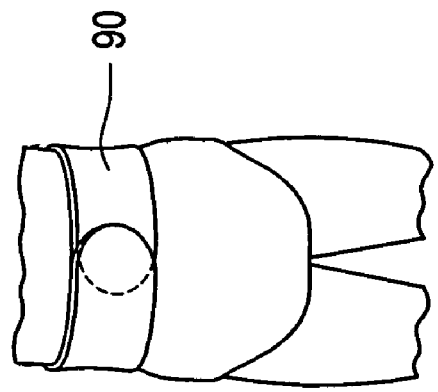
FIG. 1 is an exemplary embodiment of a waist protection garment of the invention being placed about the torso of a wearer, for fastening in the front waist region.

Referring to FIGS. 1-3, exemplary embodiments of the waist protection garment 90 of the invention are illustrated are shown being positioned around the waist of a wearer (FIG. 1), fastened in the front waist region of the wearer (FIG. 2) and fastened in the back waist region of the wearer (FIG. 3). The waist protection garment 90 is positioned in overlapping relationship with the front and back waist edges of a disposable diaper, such as may be worn by an infant or a toddler. As illustrated, the waist protection garment 90 can be fastened at any location about the waist, depending on the consumer's desired results. For example, it can be fastened in the front waist region to (i) enhance the fit of the disposable diaper, and (ii) inhibit leakage out of the front and back waist regions of the diaper. By fastening the waist protection garment in the back waist region of the wearer in such a way that the waist protection garment covers the fasteners of the diaper, an additional advantage of inhibiting undesired removal of the diaper by the young child is achieved. Fastening the waist protection garment in the back waist region also inhibit leakages through the front and back waist sections of the diaper (particularly during sleeping in the prone position in which front waist leaks may occur).

Figure 4:
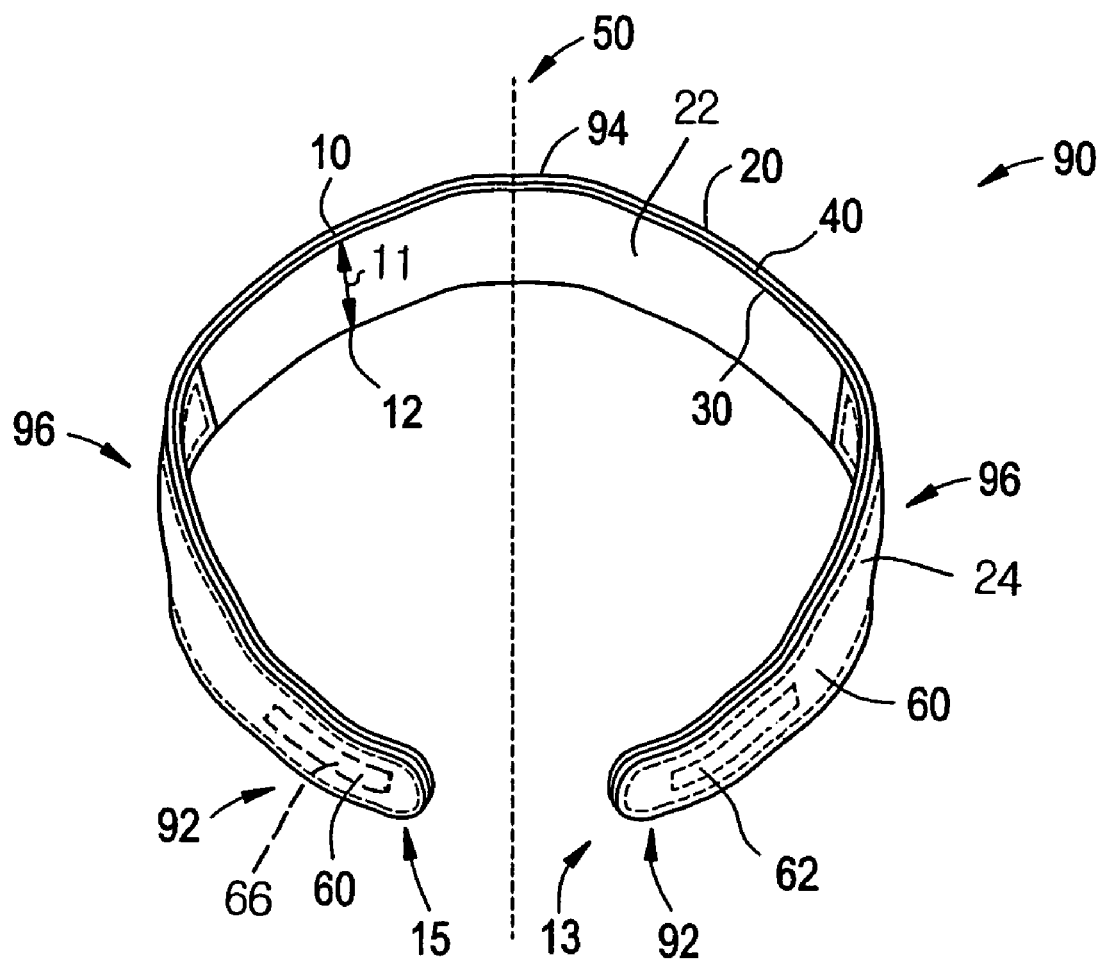
FIG. 4 is a perspective view of an exemplary embodiment of a waist protection garment of the invention.
Figure 5:
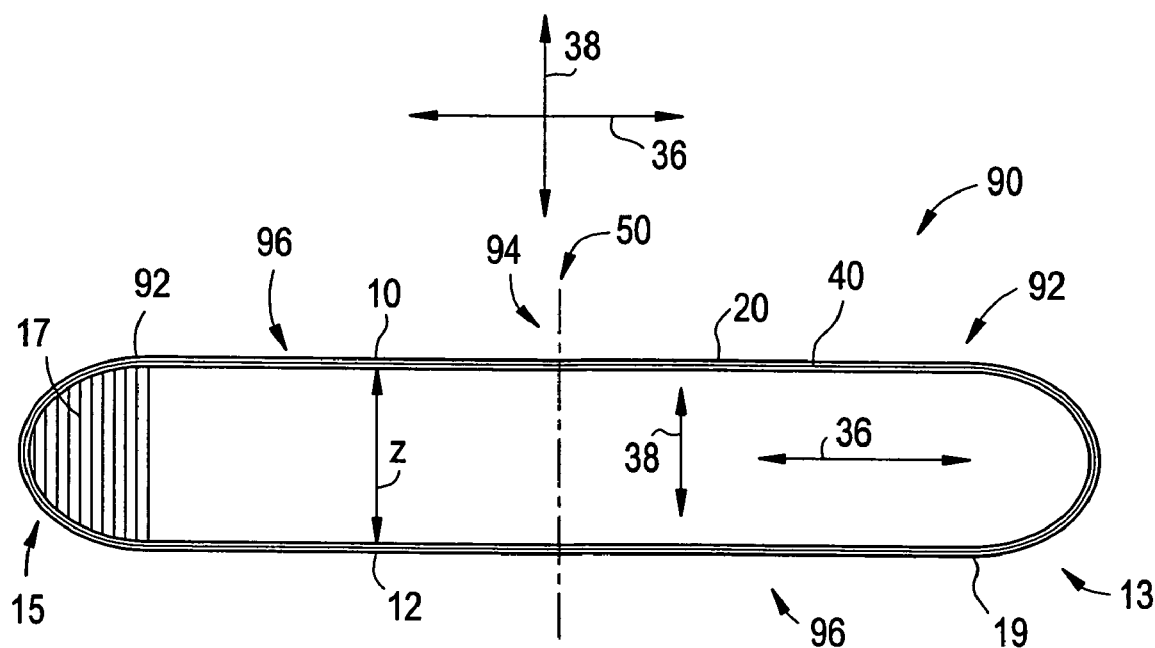
FIG. 5 is a planar view of an exemplary embodiment of a waist protection garment of the invention.

Referring to FIGS. 4 and 5, the waist protection garment 90 may include a front waistband section 92 with two opposing ends 13 and 15, a first waistband section 94, and an intermediate waistband section 96, which interconnects the front waistband section 92 and a first waistband section 94. The waist protection garment 90 may also define a length corresponding approximately to the waist circumference of a wearer where the length defines two longitudinal sides 10 and 12. Further, the waist protection garment may define a width 11 that is generally perpendicular to the length and that defines two lateral sides 13 and 15. The width 11 between the two longitudinal sides 10 and 12 is sufficient to cover the waist edges of the diaper so as to inhibit leakage inhibition. Generally, the width 11 is about 5 centimeters (cm) to about 20 cm, with 6.5 cm to about 13 cm desirable, and about 6.5 to about 9 cm more desirable. Note, all ranges disclosed herein are inclusive and combinable (e.g., ranges of less than or equal to about 25, with about 5 to about 20 desired, and about 10 to about 15 more desired, include the ranges of about 5 to about 25, about 10 to about 25, about 5 to about 15, etc.).

The length of the waist protection garment 90 (i.e., from one lateral side 13 to the other lateral side 15) is desirably at least sufficient to circumscribe the waist of the wearer. The length may be somewhat longer so that lateral sides 13 and 15 of the waist protection garment 90 may overlap (wherein enabling varying degrees of overlap enables the waist protection garment 90 to be adjustable) and be secured to each other. However, the lateral sides may merely attach to the diaper without overlapping. If the waist protection garment 90 is constructed of stretchable materials, the length of the waist protection garment when it is "relaxed" (i.e. no force pulling on it to extend) may be less than the waist circumference of the intended wearer. When the stretchable waist protection garment 90 is applied to a wearer, the stretchable materials permit the length to extend and fully encircle the wearer's waist. For many sizes of wearers, the waist protection garment 90 may have a length of between about 15 cm to 200 cm. For use with an infant diaper, the waist protection garment 90 may have a length of about 15 cm to 50 cm, with a length of about 15 cm to 40 cm preferred. For use with an adult incontinence article, the waist protection garment 90 may have a length of about 40 cm to 200 cm, with a length of about 50 cm to 125 cm desirable.

The longitudinal edges 10 and 12 may be bonded through the use of ultrasonic, thermal or adhesive bonding in order to prevent the longitudinal edges 10 and 12 from becoming frayed. The waist protection garment 90 may have different lengths for the longitudinal edges 10 and 12 so that the waist protection garment 90 may be curvilinear and arcuate in the same direction, allowing the top edge of the waist protection garment 90 to more closely conform to the wearer. The waist protection garment 90 may be arcuate so that either of the longitudinal edges 10 or 12 of the waist protection garment 90 may be longer than the other longitudinal edge of the waist protection garment 90. This generally provides a closer-fitting waist protection garment 90, which more discretely conforms to the contours around the torso of the wearer and is therefore less noticeable under clothing.

The waist protection garment 90 may be considered in terms of being divided by an imaginary longitudinal centerline 50 that divides the garment into two segments that may be identical or different. The waist protection garment 90 extends longitudinally outwards from the longitudinal centerline 50 in opposite directions, ending with the two lateral sides 13 and 15, forming the front waistband sections 92 and the first waistband section 94. The longitudinal edges 10 and 12 of the waistband sections 92 and 94 may be coplanarly arcuate within the plane of the waist protection garment 90 and concave in a first direction. When the waist protection garment 90 is worn in its desired orientation, the first direction is concave upward such that the lateral sides 13 and 15 are disposed higher on the wearer's body than the location of the longitudinal centerline 50.

The front waistband section 92 and the first waistband section 94 may project generally rectilinearly from the centerline 50. The front waistband section 92 may have a length along the longitudinal edges 10 and 12 of greater than or equal to about 10 centimeters to less than equal to about 26 centimeters.

Referring to FIG. 5, the waist protection garment 90 may generally be rectilinear, curvilinear, or a combination of both, in shape, and may be sized to fit a variety of wearers. In order to allow the waist protection garment 90 to be adjustable, it may have a landing zone 19 that extends for several centimeters from the lateral side 13 on either the bodyfacing surface 22 or the outer surface 24 of the waist protection garment 90. For example, the landing zone 19 may extend for about 1 to about 15 centimeters from the lateral side 13, along the outer surface 24 of the waist protection garment 90. Meanwhile, a fastener 17 may be disposed at or near the opposite lateral side 15 such that when the waist protection garment 90 is disposed about a wearer's waist, fastener 17 engages the landing zone 19. The length of the landing zone 19 and its exact location are dependent upon the desired adjustability of the waist protection garment 90. Generally, the landing zone 19 may be disposed at or near the lateral side 13 (i.e., adjacent the lateral side 13), and may have a length of about 2 cm to about 10 cm. The fastener 17 has a sufficient size and geometry to engage the landing zone 19 and to retain the waist protection garment 90 about the wearer's waist. The fastener 17 may include a hook material, such as those that are presently used with the fasteners of commercially-available disposable diapers.

Referring to FIG. 4, the waist protection garment 90 may have a multilayer structure including an outer cover 20, an optional absorbent core 40, and a liner 30. The liner 30 is in superposed relation to the outer cover 20 and defines a bodyfacing surface 22. The outer cover 20 may be a single layer of a fluid impermeable material, and may or may not have vapor permeability. The outer cover 20 may be constructed of any suitable material(s) that either directly provides the desired levels of liquid impermeability and air permeability or, in the alternative, a material that can be modified or treated in some manner to provide such levels. In one aspect, the outer cover 20 may be a nonwoven fibrous web constructed to provide the required level of liquid impermeability. For example, a nonwoven material including spunbond or meltblown polymer fibers may be selectively treated with a water repellent coating or laminated with a fluid impermeable, vapor permeable polymer film to provide the outer cover 20. More specifically, the outer cover 20 may include a nonwoven web composed of a plurality of randomly deposited fluid impermeable thermoplastic meltblown fibers that are sufficiently bonded or otherwise connected to one another to provide a substantially vapor permeable and substantially fluid impermeable web. The outer cover 20 may also include a vapor permeable nonwoven layer that has been partially coated or otherwise configured to provide liquid impermeability in selected areas.

Examples of suitable materials for the outer cover 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. Pat. No. 5,879,341 issued Mar. 9, 1999 in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE BACKSHEET"; and U.S. Pat. No. 6,075,179 issued Jun. 13, 2000, in the name of McCormack et al. and entitled "LOW GAUGE FILMS AND FILM/NONWOVEN LAMINATES".

The outer cover 20 may be provided by a stretchable material, such as an extensible or elastic material. For example, the outer cover 20 may be provided by a material being elastic in one or both of the longitudinal 36 and lateral 38 directions of the waist protection garment 90. When the outer cover 20 is made from stretchable materials, the waist protection garment 20 provides additional benefits to the wearer including enhanced fit. Elastomeric materials (such as stretch-thermal laminate (STL), a neck-bonded laminate (NBL), or a stretch-bonded laminate (SBL) material may be used to form the outer cover 20. Methods of making such materials are well known to those skilled in the art and are described in U.S. Pat. No. 4,663,220, issued May 5, 1987 to Wisneski et al., U.S. Pat. No. 5,226,992, issued Jul. 13, 1993 to Morman; and European Patent Application No. EP 0 217 032 published Apr. 8, 1987 in the names of Taylor et al., the disclosures of which are incorporated herein by reference. The outer cover 20 may be embossed or otherwise provided with a matte finish to provide a more aesthetically-pleasing appearance.

The liner 30 may include a substantially liquid permeable sheet employed to help absorb leakage from the diaper. The liner 30 may include an absorbent cellulosic material, such as creped wadding or a high wet-strength tissue. The liner 30 may also include various types of wettable, liquid permeable fibrous materials. Some examples of suitable materials, include naturally-occurring organic fibers composed of intrinsically wettable material, such as cellulosic fibers; synthetic fibers composed of cellulose or cellulose derivatives, such as rayon fibers; inorganic fibers composed of an inherently wettable material such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means. The liner 30 may also include a mixture comprising at least one of the above mentioned materials.

The liner 30 may also be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The liner 30 is suitably employed to help isolate the wearer's skin from liquids held in the absorbent core 40. The liner 30 can also be made from extensible materials as are described in U.S. Pat. No. 6,552,245 issued on Apr. 22, 2003 to Roessler et al. The liner 30 can also be made from biaxially stretchable materials as are described in International Publication No. WO 02/34184 by Vukos et al.

Various woven and nonwoven fabrics can be used for the liner 30. For example, the liner 30 may be composed of a meltblown or spunbond web of polyolefin fibers. The liner 30 may also be a bonded-carded web composed of natural and/or synthetic fibers. The liner 30 may be composed of a substantially hydrophobic material, and the hydrophobic material may optionally be treated with a surfactant or otherwise processed to impart a desired level of wettability and hydrophilicity. In a particular embodiment of the present invention, the liner 30 is made from a nonwoven, spunbond, polypropylene fabric composed of fibers having a fiber diameter of about 21 to 23 microns formed into a web having a basis weight of about 20 grams per square meter and a density of about 0.13 grams per cubic centimeter. The fabric may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The liner 30 may further include a lotion or treatment applied thereto that is configured to be transferred to the wearer's skin. Suitable compositions for application to the liner 30 are described in U.S. Pat. No. 6,149,934 that issued to Krzysik et al. on Nov. 21, 2000.

The waist protection garment 90 may have an improved fit range performance when a stretchable outer cover 20 and a stretchable liner 30 are matched. The fit range performance of the waist protection garment 90 may be measured in Percent Fit Range. Desirably, the Percent Fit Range of the waist protection garment 90 is greater than or equal to about 33%, more desirably about 50% to about 200%, with about 80% to about 150% even more desirable. The Percent Fit Range ("PFR") of the waist protection garment 90 is measured using the following Equation (1):

$$PFR = (WP_e - WP_r) \times 100 / WP_r$$ Eq. (1)

wherein $WP_e$ is an extended waist performance measurement of the waist protection garment 90 and $WP_r$ is a relaxed waist performance measurement of the waist protection garment 90. When measuring the Percent Fit Range of the waist protection garment 90, the fastener 17 is engaged as it will be employed during use (if the waist protection garment 90 does not have a fastener 17—such as when the waist protection garment 90 is a continuous band of material(s), this does not apply). The extended waist performance measurement and the relaxed waist performance measurement of the waist protection garment 90 are dependent upon many factors, including the age and size of the wearer. The extended waist performance measurement is measured when the waist protection garment 90 is extended in the longitudinal direction (see FIG. 9, arrow 36) by a force of about 1,400 grams (g). This force is applied using the equipment described in U.S. patent application Ser. No. 09/827,192 filed on Apr. 5, 2001 by Popp et al. (the equipment is representatively illustrated in FIG. 8 of the application). This applied force is comparable to a maximum comfortable tension force of the waist protection garment 90 against the wearer's torso during use. The relaxed waist performance measurement is measured when the waist protection garment 90 is longitudinally extended by a force of about 80 grams to about 100 grams. This applied force is comparable to a minimum tension force required to maintain the waist protection garment 90 in proper wearing position on the wearer. In comparison, a typical tension force applied to the waist protection garment 90 during use is about 400 grams.

To provide a desired Percent Fit Range of at least about 33%, the waist protection garment 90 includes components that are stretchable in the longitudinal direction 36. Cost-effective elastic materials, as well as additional extensible materials which do not limit or restrict the elastic materials, determine the Percent Fit Range of the waist protection garment 90.

In addition to employing stretchable materials to form the outer cover 20 and the liner 30 to achieve the desired Percent Fit Range, elastic materials that may generally be made of natural rubber, or an elastomeric material such as isoprene purchasable from JPS Elastomerics Company, Holyoke, Me. may be incorporated into the waist protection garment 90. The elastic materials may be a single ribbon of material, or a plurality of strands or ribbons of elastic material, for example, LYCRA® 940 decitex, which may be purchased from E.I. DuPont de Nemours Company, Wilmington, Del. The elastic material may be in sheets, strands or ribbons of a polymeric, elastomeric material that may be disposed through and/or adhered to the outer cover 20 or to the liner 30 in a stretched position.

An absorbent core 40 may be interposed between the outer cover 20 and the liner 30 along at least a portion of the waist protection garment 90. The absorbent core 40 may aid in the absorption and containment of any waste that leaks through the waist edges of the diaper. The absorbent core 40 may also be encased in a tissue wrap, in order to maintain the integrity of the absorbent material. Optionally, more than one absorbent core 40 may be disposed along the length of the waist protection garment 90 in strategic locations to provide maximum absorption.

The absorbent material in the absorbent core 40 can include natural, synthetic, and modified natural polymers and materials, as well as combinations comprising at least one of the foregoing absorbent materials. A suitable natural absorbent material is a wood pulp fluff identified by the trade designation CR 1654 from Bowater. This particular wood pulp fluff is a bleached, absorbent wood pulp fluff. The absorbent materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, liquid permeable associations such as hydrogen bonding, and fluid impermeable associations or Van der Waals forces.

Examples of synthetic, polymeric, absorbent materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers comprising at least one of the foregoing absorbent materials. Further polymers suitable for use in the absorbent core 40 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Suitable superabsorbent materials are available from various vendors, such as Stockhausen Inc., Dow Chemical Company, and BASF. Generally, the superabsorbent material may be capable of absorbing greater than equal to about 15 times its weight in water, and may generally be capable of absorbing greater than equal to about 25 times its weight in water. Mixtures including at least one of any of the above absorbent materials can also be employed.

In general, the superabsorbent material may be in the absorbent core 40 in an amount of about 5 to about 90 weight percent, desirably in an amount of greater than or equal to about 30 weight percent, and even more desirably in an amount of greater than or equal to about 50 weight percent based on a total weight of the absorbent core 40.

The absorbent core 40 may be configured to contain and/or absorb any body exudates discharged by the wearer. The absorbent core 40 may generally be conformable and capable of absorbing and retaining the body exudates.

Alternatively, or in addition, absorbent material including a foam and/or other conformable, desirably resilient, material(s) may be employed in strategic locations around the waist protection garment 90. The conformability of the absorbent assists in the leakage protection ability of the waist protection garment 90, for example by reducing or eliminating the gap at the back waist of the wearer. The gap is formed by the curvature of the wearer's body at the small of the back.

The various layers (e.g., outer cover layer 20, liner 30, and/or absorbent core 40) can be retained together by various techniques, including the use of adhesives or ultrasonic bonding. Adhesives may be any material suitable for joining the identified layers and/or materials. Suitable adhesives may be obtained, for example, from Findley Adhesives, Inc. Wauwatosa, Wis. or may be obtained from National Starch and Chemical Co., Bridgewater, N.J. The adhesives may be in any desired configuration, such as continuous or discontinuous beads, continuous or discontinuous swirls, meltblown patterns, spray patterns, and similar configurations. The application of adhesive may generally be accomplished by partially or totally coating the mutually facing surfaces of the adjacent layers, or by applying the adhesive in a bead to at least one of the layers. The latter method may usually involve a continuous bead pattern, such as a wave-like pattern of adhesive.

The waist protection garment 90 may have a fastening system 60. The fastening system 60 may be attached to the two laterally opposing front waistband sections 92 of the waist protection garment 90 having two lateral sides 13 and 15 at either end of the waist protection garment 90. The fastening system 60 may be releasably engageable allowing for securing and removing the waist protection garment 90, from the torso of the wearer. For example, the waist protection garment 90 may be adjustable in such a way that a waist protection garment 90 of a given length may be used with children of different waist circumferences, but within a similar size range (e.g. the same diaper size, which accommodates children within a range of weight). In an exemplary aspect, a fastener that may be located near one of the lateral sides, e.g. lateral side 15, and may be releasably engageable directly with the outer surface 24 of the outer cover 20 to provide improved ease of fastening. The fastening system 60 may extend from and/or be disposed at/near (hereinafter "at") one or both lateral sides 13 and 15 of the waist protection garment 90, or hang therefrom. The fastening system 60, of the waist protection garment 90 may include any suitable fastener such as adhesive tape tab fasteners, hook and loop fasteners, mushroom fasteners, snaps, pins, and the like, and combinations thereof. A particular example of a releasable attachment system is a hook and loop (also called touch and close) fastening system 60, such as sold by Velcro Industries. In an exemplary embodiment, referring to FIG. 4 the fastening system 60 may be a relatively long strip of fastener material 62 (e.g. hook material) attached to the bodyfacing surface 22 of the front waistband section 92 near one lateral side 13. A relatively short strip 66 of cooperating fastener material (e.g. loop material) is affixed to the outer surface 24 of the front waistband section 92 near the opposite lateral side 15. With this configuration, the fastener 62 would engage the cooperating fastener 66.

The relatively long and short strips 62 and 66 (17 and 19 of FIGS. 5-8) may be of any suitable mutually engagement material, the components of which mutually engage to each other, when in contact (but preferably do not adhere to different materials). Generally, such engagement materials include a first material component presenting a surface of closely spaced looped filaments and a second material component presenting a surface of hook-like projections. When placed in contact, the hook-like projections engage the looped filaments to provide a firm connection while permitting the cooperating materials to be pulled apart.

Alternatively, the waist protection garment 90 can comprise an adhesion area disposed adjacent (i.e., at or near) both lateral sides 13 and 15, and on one side of the waist protection garment 90 (i.e., on the outer cover 20, or on the liner 30). In this alternative, the lateral sides 13 and 15 would not overlap during use. They would engage the absorbent article to provide the desired leakage prevention, etc.

To ensure proper location of the waist protection garment 90 and maintenance of the garment 90 over the edges of the absorbent article, an optional additional attachment mechanism may be employed such that the waist protection garment 90 could engage the absorbent article. For example, hooks may be arranged on at least a portion of the bodyfacing surface 22 near a longitudinal side 10 or 12 that will come into contact with the landing zone of the diaper (i.e., the location where the diaper fasteners attach to the outer cover of the diaper) when the waist protection garment 90 is donned. Alternatively, the attachment mechanism may engage the outer layer of the absorbent article, such as along the waist edge of the back waist region of the absorbent article. The lateral sides 13 and 15 could fit into opening(s) (e.g., slit(s) or the like) in the diaper or incontinence article to enable proper location of the waist protection garment 90 and attachment.

Figure 9:
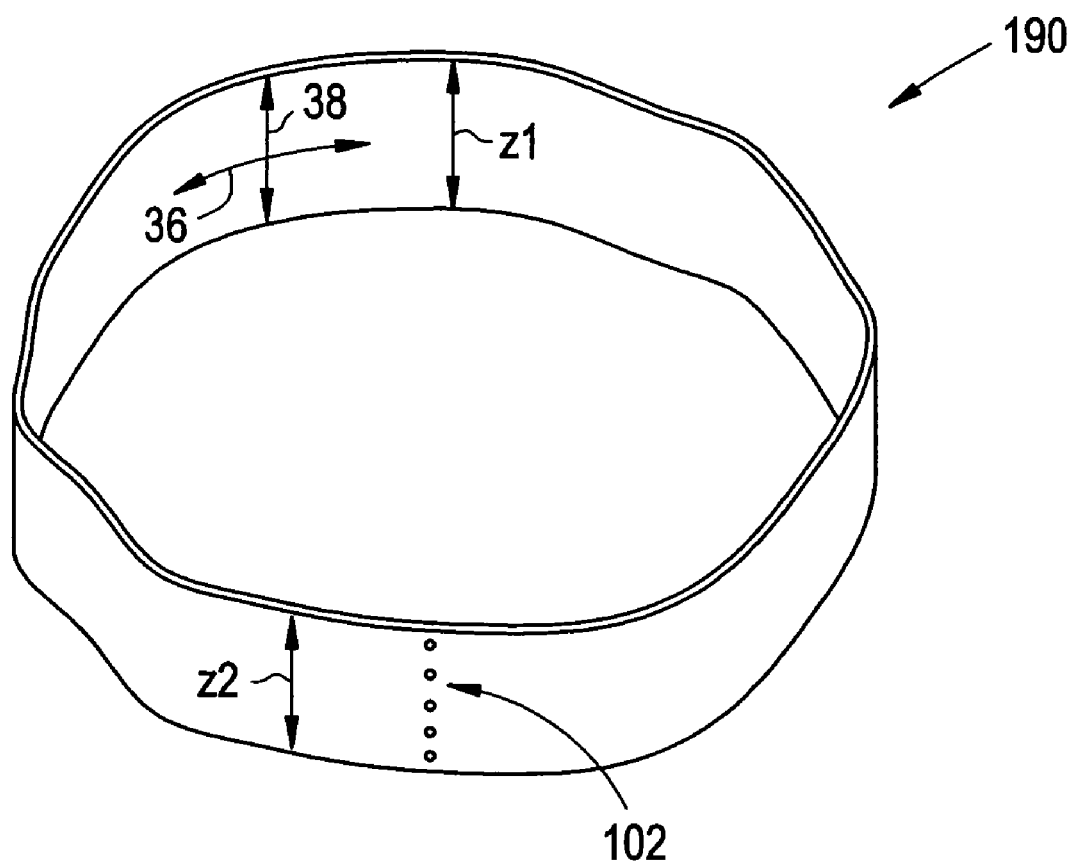
FIG. 9 is a perspective view of an exemplary embodiment of an annular waist protection garment of the invention.

In a different aspect of the present invention, the waist protection garment 190 may be in the form of a continuous band or ring, such as that shown in FIG. 9. The length of the continuous band generally corresponds to the waist circumference of the wearer. In this aspect, the waist protection garment 190 has sufficient stretchability to enable it to be placed around the waist of the wearer by sliding it over the head of the wearer and moving it down the body into location or by sliding it up from the wearer's feet. This aspect may also include an adjustment mechanism to enable the garment to be tightened about the waist of the wearer. The waist protection garment 190 depicted in FIG. 9 has a varied or non-uniform width over the length of the waist protection garment 190. For example, the waist protection garment may have a width, z1, designed to be located over the back waist region of the wearer and a width, z2, designed to be located over the front waist region of the wearer. The widths, z1 and z2, are generally perpendicular to the circumference of the waist protection garment 190.

The waist protection garment 190 may include one or more frangible section(s), such as passive bond(s), perforation(s) or perforation line(s). The perforations or perforation lines 102 may be formed by a pre-stressed or thinned section of material, a score line, a section of different, weaker material, or other configurations adapted to be readily torn or broken in order to separate the material. The passive bonds and/or perforations facilitate removal of the waist protection garment 190 after use. The frangible section 102 may not extend completely across the width of the waist protection garment 190, but may desirably be present in a degree sufficient to allow the appropriate material, as well as adjacent material, to be easily torn or broken. Alternatively, the frangible section 102 may extend across a majority of the width z1 or z2. The frangible section 102 may have a linear or a non-linear configuration. Examples of non-linear configurations include: an arcuate shape, a curved shape, a saw-toothed shape, a sinusoidal shape or a zigzag shape. The frangible section 102 may be formed of intermittent strength along the width of the waist protecting garment 190 by making some areas stronger than other areas. This feature may assist in assuring that the frangible section 102 will not tear prematurely when the waist protection garment 190 is placed around the wearer's torso. This feature may also provide a frangible section 102 that is more easily broken in order to start the opening process.

Since the waist protection garment 90 is a separate component from the absorbent articles with which it may be used, and since it does not contact any bodily fluids (unless there is leakage from the absorbent article), the waist protection garment 90 may be reused. Optionally, the liner 30 and the outer cover 20 of the waist protection garment 90 may include material(s) capable of being laundered such that even a soiled waist protection garment 90 can be reused.

Advantageously, use of the waist protection garment 90 assists to make the diaper or other absorbent article be tamper proof and prevents opening by accident. If the outer cover 20 of the waist protection garment 90 includes a stretchable material, the waist protection garment may provide an improved fit of the diaper in the waist regions. If provided, the absorbent core 40 of the waist protection garment may eliminate waist leakage. As shown in FIG. 3, the waist protection garment 90 may be worn such that its opening lands over the back waist region of the wearer.

Figure 6:
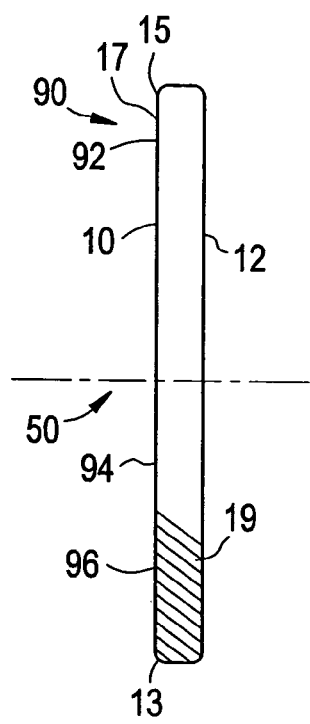
FIG. 6 is a planar view of an exemplary embodiment of a rectilinear waist protection garment of the invention.
Figure 7:
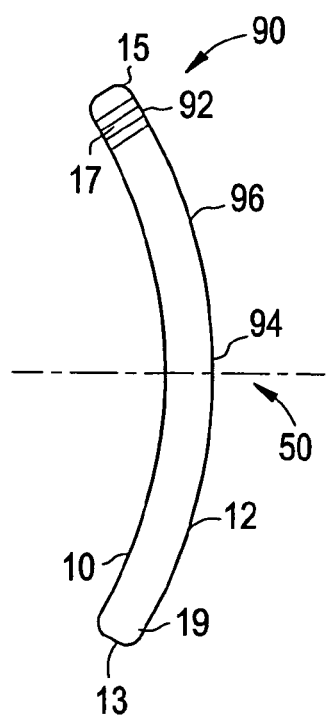
FIG. 7 is a planar view of an exemplary embodiment of a curvilinear waist protection garment of the invention.
Figure 8:
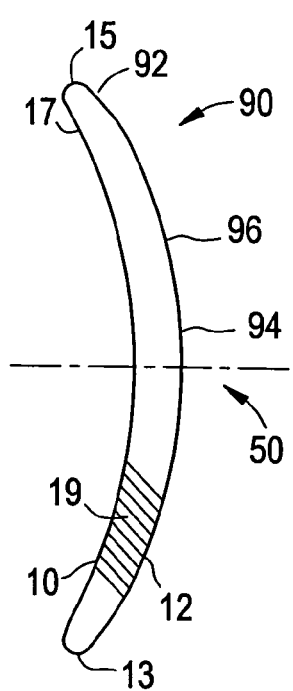
FIG. 8 is a planar view of an exemplary embodiment of a rectilinear and curvilinear waist protection garment of the invention.

Other variations of the waist protection garment are feasible. For example, as shown in FIGS. 6-8 the arcuate longitudinal edges of the waist protection garment 90 may be rectilinear (as shown in FIG. 6) or curvilinear (as shown in FIG. 7). The longitudinal edges 10 and 12 may also include two or more adjacent or juxtaposed discrete rectilinear segments, or adjacent rectilinear and curvilinear segments (as shown in FIG. 8). The specific geometry of the waist protection garment 90 is dependent upon the size and shape of the end-user, and the ultimate use (e.g., for a child wearing a diaper or for an adult wearing an incontinence article). Regardless of the shape of the longitudinal edges 10 and 12, the longitudinal edges 10 and 12 may include fasteners near or adjacent the edges. The fasteners along the longitudinal edges may provide for additional attachment between the waist protection garment 90 and the absorbent article with which the waist protection garment is being used.

While the invention has been described with reference to an exemplary aspects, it will be understood by those skilled in the art that various changes may be made and equivalents may be substituted for elements thereof without departing from the scope of the invention. In addition, many modifications may be made to adapt a particular situation or material to the teachings of the invention without departing from the invention scope thereof. It is therefore intended that the invention not be limited to the particular embodiment disclosed as the best mode contemplated for carrying out this invention, but that the invention will include all embodiments falling within the scope of the appended claims.

We claim:

1. A leakage containment system, comprising:
an absorbent article comprising a front waist region and a back waist region; and
a waist protection garment capable of being disposed over at least one of the front waist region and the back waist region when the absorbent article is worn, the waist protection garment comprising a length corresponding to the waist circumference of a wearer, the length defining two longitudinal sides; a width in a direction perpendicular to the length, the width defining two lateral sides; an outer cover comprising a fluid impermeable material; a liner in superposed relation to the outer cover, the liner defining a bodyfacing surface and comprising a liquid permeable material; and a fastener for attaching one lateral side to the other lateral side.

2. The leakage containment system of claim 1, further comprising an absorbent core disposed between the liner and the outer cover.

3. The leakage containment system of claim 1, wherein the outer cover includes a stretchable material and the liner includes a stretchable material.

4. The leakage containment system of claim 1, wherein the length is capable of elongating by 50% to 200% at a load of less than or equal to about 700 g.

5. The leakage containment system of claim 1, wherein the fastener comprises a hook material.

6. The leakage containment system of claim 1, further comprising a landing zone on the lateral side of the waist protection garment opposite the fastener.

7. The leakage containment system of claim 1, wherein the length is about 15 cm to 200 cm.

8. The leakage containment system of claim 1, wherein the width is about 5 cm to 20 cm.

9. The leakage containment system of claim 1, further comprising an attachment mechanism disposed on at least a portion of at least one of the longitudinal sides.

10. The leakage containment system of claim 1, wherein the width is not uniform.

11. The leakage containment system of claim 1, wherein the waist protection garment has a Percent Fit Range of greater than or equal to about 33%.

12. A leakage containment system, comprising:
- an absorbent article comprising a front waist region and a back waist region; and
- a waist protection garment capable of being disposed over at least one of the front waist region and the back waist region when the absorbent article is worn, the waist protection garment comprising a circumference corresponding to the waist circumference of a wearer, the circumference defining two longitudinal sides; a width in a direction perpendicular to the circumference; a stretchable outer cover comprising a fluid impermeable material; and a stretchable liner in superposed relation to the outer cover, the liner defining a bodyfacing surface and comprising a liquid permeable material.

13. The leakage containment system of claim 12, further comprising a passive bond across the width.

14. The leakage containment system of claim 12, further comprising a perforation across the width.

15. The leakage containment system of claim 12, further comprising a fastener on at least one of the longitudinal sides.

16. The leakage containment system of claim 12, further comprising an absorbent core disposed between the liner and the outer cover.

* * * * *